(12) United States Patent
Bürgin et al.

(10) Patent No.: US 11,365,384 B2
(45) Date of Patent: Jun. 21, 2022

(54) WATER BATH FOR HUMIDIFYING AN INTERIOR OF AN INCUBATOR

(71) Applicant: Adolf Kühner AG, Birsfelden (CH)

(72) Inventors: Timothy Bürgin, Liestal (CH);
Mathias Schumacher, Lörrach (DE);
Simon Knobel, Pratteln (CH)

(73) Assignee: ADOLF KÜHNER AG, Birsfelden (CH)

( * ) Notice: Subject to any disclaimer, the term of this patent is extended or adjusted under 35 U.S.C. 154(b) by 0 days.

(21) Appl. No.: 16/990,160

(22) Filed: Aug. 11, 2020

(65) Prior Publication Data
US 2021/0047603 A1    Feb. 18, 2021

(30) Foreign Application Priority Data
Aug. 12, 2019   (DE) ................. 10 2019 121 639.7

(51) Int. Cl.
| | |
|---|---|
| *C12M 3/00* | (2006.01) |
| *C12M 1/00* | (2006.01) |
| *C12M 1/12* | (2006.01) |
| *C12M 1/02* | (2006.01) |

(52) U.S. Cl.
CPC ............ *C12M 41/14* (2013.01); *C12M 25/06* (2013.01); *C12M 41/24* (2013.01)

(58) Field of Classification Search
CPC .............................. C12M 41/14; C12M 25/06
See application file for complete search history.

(56) References Cited

U.S. PATENT DOCUMENTS

| | | | | |
|---|---|---|---|---|
| 3,664,324 A | * | 5/1972 | Radtke | ............ F24H 1/00 126/113 |
| 4,399,080 A | * | 8/1983 | Swank | ............ F24F 6/06 128/200.17 |
| 4,923,816 A | | 5/1990 | Heeg | |
| 5,514,299 A | * | 5/1996 | Kalwara | ............ B65D 90/46 220/23.87 |
| 5,890,703 A | | 4/1999 | Kaus | |
| 6,099,461 A | | 8/2000 | Maresch | |
| 7,867,762 B2 | | 1/2011 | Stahl | |
| 10,619,129 B2 | | 4/2020 | Cesana | |
| 2002/0007155 A1 | * | 1/2002 | Freund | ............ B65D 83/62 604/232 |
| 2011/0117285 A1 | * | 5/2011 | Morrison | ............ F24H 1/183 427/470 |

(Continued)

FOREIGN PATENT DOCUMENTS

| | | |
|---|---|---|
| DE | 3815528 C1 | 8/1989 |
| DE | 102011121019 A1 | 6/2013 |

(Continued)

*Primary Examiner* — Nathan A Bowers
(74) *Attorney, Agent, or Firm* — Lucas & Mercanti, LLP

(57) ABSTRACT

To avoid cleaning costs and to reduce the risk of cross-contamination, a water bath for use in incubators includes a profiled receiver, open at least at the upper face, preferably at the end faces and the upper face, with receiver surfaces extending in the longitudinal direction. A prefabricated disposable vessel for liquid open at the upper face includes vessel walls that lie flush on the receiver surfaces of the receiver. Fastenings are used fix the disposable vessel on the receiver. The water bath also includes a liquid supply, designed for filling the disposable vessel with liquid.

11 Claims, 4 Drawing Sheets

(56) References Cited

U.S. PATENT DOCUMENTS

| | | | |
|---|---|---|---|
| 2011/0189765 A1* | 8/2011 | Fukui | C12M 23/48 435/303.1 |
| 2013/0146104 A1 | 6/2013 | Stahl | |
| 2014/0356934 A1 | 12/2014 | Barka | |
| 2016/0165831 A1* | 6/2016 | Adams | A01K 1/0125 119/170 |
| 2017/0297816 A1* | 10/2017 | Esomeju | B65F 1/1405 |

FOREIGN PATENT DOCUMENTS

| | | |
|---|---|---|
| DE | 102013009136 A1 | 12/2014 |
| DE | 102017104508 B3 | 3/2018 |
| DE | 102017118729 A1 | 2/2019 |
| EP | 0808657 A2 | 11/1997 |
| EP | 0808657 B1 | 11/1997 |
| EP | 0913199 B1 | 1/2003 |
| EP | 1552888 A2 | 7/2005 |
| EP | 2573162 A1 | 3/2013 |
| JP | 2017123786 A | 7/2017 |

* cited by examiner

WATER BATH FOR HUMIDIFYING AN INTERIOR OF AN INCUBATOR

CROSS-REFERENCE TO RELATED APPLICATIONS

The present application claims priority under 35 U.S.C. § 119 to German Patent Application DE 10 2019 121 639.7, filed on Aug. 12, 2019, the entire contents of which are incorporated herein by reference.

BACKGROUND OF THE INVENTION

The invention relates to a water bath for humidifying an interior of an incubator.

By humidifying the gas mixture in the interior of the incubator, evaporation of cell culture medium from one or more vessels is reduced and, in this way, an evaporation-induced concentration of substances in the cell culture medium is prevented.

However, the humidifying promotes the multiplication of microorganisms on surfaces within the interior of the incubator, even when these surfaces are made of stainless steel. The humid and wet surfaces in an incubator are potential contamination sources that may destroy the cell culture.

This applies in particular to the surfaces of a water bath, from the water surface of which heated water evaporates directly into the interior of the incubator and humidifies the gas mixture in the interior of the incubator.

Water baths therefore have to be manually cleaned on a regular basis, which is laborious work. For this purpose, the water bath has to be emptied, removed from the incubator, cleaned with disinfecting cleaning agents, and then flushed with water. It is often the case that deposits, for example limescale, also have to be removed mechanically from the surface of the water bath.

EP 0 913 199 B1 discloses a device for humidifying the working space of a climatic cabinet, which device reduces the danger of contamination, by permitting optimum cleaning of the water container, and excludes or at least reduces the danger of condensate forming outside the water container. The working space is inserted as an inner housing obliquely into an outer housing of the climatic cabinet. The lower region of the working space serves to receive water in the manner of a trough with an inclined floor surface, wherein the slope is in the direction of the rear wall of the working space.

DE 10 2013 009 136 A1 discloses an incubation chamber with a moisture reservoir, a climate control device, which makes it possible to set a desired temperature, and a holder for specimens. The moisture reservoir is preferably designed as a trough, of which the active surface is enlarged by a felt or foam layer or by other water-storing substances. The climate control device has two separate climate control zones, which are able to be regulated separately from each other. This is intended to create reproducible conditions in the incubation chamber.

EP 0 808 657 B1 discloses a container which is closed on all sides, is delimited by water-tight walls and serves to receive water, said container being made at least in part of a material that is permeable to water vapor but impermeable to liquid water. The container is used for humidifying climatic cabinets. To minimize the risk of contamination, the container is designed as a flexible bag which can be refilled through a closure, wherein at least the water-vapor-permeable part of the flexible bag has an enlarged surface area in relation to a smooth and structured surface. The filling of the flexible bag preferably takes place outside the climatic cabinet. The structured and thereby enlarged surface is proposed in order to avoid the large and open evaporation surfaces which are common in the prior art and which are regarded as a contamination risk the longer they are in use. The bag can be suspended in the climatic cabinet or can be laid in a trough.

JP 2017 123786 A has likewise disclosed a humidifying bag for an interior of an incubator, which humidifying bag is filled, prior to use, with sterile water via an opening that is to be welded, said water evaporating into the interior of the incubator through a water-impermeable but gas-permeable membrane in the bag. To prevent evaporation of the water prior to the use of the humidifying bag, the opening in the bag, said opening having the membrane, is provided from outside with a releasable self-adhesive cover. The humidifying bag can be laid in a depression formed in the floor of the incubator.

BRIEF SUMMARY OF THE INVENTION

Proceeding from this prior art, an object of the invention is to provide a water bath for use in incubators, which water bath does not require cleaning and reduces the risk of cross-contamination.

This object is achieved by a water bath for humidifying an interior of an incubator, the water bath including a profiled receiver, open at least at the upper face, but preferably at the end faces and the upper face, with receiver surfaces extending in the longitudinal direction, a prefabricated disposable vessel for liquid, open at the upper face, and having vessel walls that lie flush on the receiver surfaces of the receiver, fastenings for fixing the disposable vessel on the receiver, and a liquid supply designed for filling the disposable vessel with liquid.

After use, the disposable vessel for liquid, open at the upper face, is replaced by a new disposable vessel. This dispenses with the need for cleaning work and cleaning validation. This saves time and therefore also reduces costs. Moreover, the disposable vessel reduces the danger of cross-contamination. A further advantage is that the environmental burden posed by the disposable vessel in biopharmaceutical production is less than the environmental burden posed by cleaning and sterilizing a conventional water bath made of stainless steel. During cleaning and sterilizing, large quantities of cleaning agents, some of them petroleum-based agents, and a great deal of energy are consumed.

The receiver is the component part of the water bath that is not disposed of after use. The receiver is made of stainless steel, for example. However, it can also be made of other materials, such as aluminum or copper. If the receiver is open at the end faces, the disposable vessel can protrude in the longitudinal direction beyond the receiver surfaces. By the protrusion of the disposable vessel, or by the end faces of the disposable vessel also being adapted to the shape of the receiver, it is ensured that the entire surface area of the receiver surfaces is in contact with the disposable vessel. This is of importance in particular when the receiver surfaces of the receiver are heated. This therefore avoids a situation in which partial surface areas of the receiver surfaces are not in contact with the vessel walls and there is an undesired input of heat from the heated receiver surfaces into the interior of the incubator.

The disposable vessel is open to the interior of the incubator at the upper face, such that the water surface comes directly into contact with the gas mixture in the interior.

The disposable vessel is used for a defined period of time, e.g., a few days to several weeks, and is thereafter disposed of and then replaced by a new one. The disposable vessel is entirely prefabricated. Prefabricated means that the disposable vessel can be used directly by the user without any further working.

Since the vessel walls lie flush on the receiver surfaces, contamination in spaces between the receiver and the disposable vessel is avoided.

The fastenings permit exact positioning of the disposable vessel on the receiver and optimum contact between the receiver surfaces and the vessel walls.

The liquid supply permits both the initial filling of the water bath, for example via a water port of the incubator, and also refilling of liquid during the operation of the incubator.

The disposable vessel is preferably made of a flexible material, e.g., a single-layer or multi-layer flexible film of thermoplastic, i.e., weldable plastic. In principle, however, the disposable vessel can also be a rigid shaped plastic part adapted to the receiver. The disposable vessel can be sterile or non-sterile. The sterilization is effected, for example, by ethylene oxide sterilization or gamma ray sterilization.

To be able to produce the disposable vessel cost-effectively, with the smallest possible amount of material and with a small number of work steps, an advantageous embodiment of the invention is proposed in which a disposable vessel has a substantially rectangular film which is folded along a longitudinal mid-line and, at the end faces, is provided with a weld seam running from the longitudinal mid-line to the longitudinal edges of the film.

In one embodiment of the invention, a drainage tube with a shut-off member is welded into one of the two weld seams, i.e., adjacent to the longitudinal mid-line. With just two welding procedures, it is possible to produce the disposable vessel and moreover attach the drainage tube to the vessel, at the end face thereof and near the floor, in such a way as to convey liquid. The less welding that has to be carried out, the fewer the work steps that are required for producing the disposable vessel.

In an advantageous embodiment of the invention, the profiled receiver has a V-shaped cross section. The flexible disposable vessel with only two weld seams is optimally received by the V-shaped receiver. The resulting triangular profile is ideal for the water bath, since the ratio of the liquid surface area at the upper face of the receiver to the liquid volume received by the disposable vessel is greater than in a conventional water bath with a square cross section. Particularly in the case of heated water baths, a large evaporation surface for the liquid is sought, at the same time with a small volume of liquid, since a smaller quantity of liquid needs to be temperature-controlled by means of the heating. The smaller the volume of liquid, the more rapidly the liquid is heated. The large surface area of the liquid and the small volume of the liquid increase the rate of evaporation and reduce the time needed to reach the desired value for the relative humidity in the interior of the incubator. The low heating power needed to heat the small volume of liquid additionally has the advantage that the sometimes undesired input of heat through the water bath into the interior of the incubator is reduced.

If the receiver, with its V-shaped cross section, is designed as a one-piece angled profile, the limbs of the profile form the receiver surfaces. The longitudinally extending transition between the limbs of the profile is preferably rounded so that the receiver can be cleaned without any problem.

In order to heat the receiver surfaces, an advantageous embodiment of the invention is one in which heating elements are arranged on the rear of the two receiver surfaces. The heating elements are designed as electrical resistance heaters. The resistance heaters are planar and preferably have the shape of a mat. The shallow configuration of the heating elements saves space. The fastening of the heating elements to the rear can be provided by adhesive bonding, for example. The heating elements control the temperature of the liquid in the disposable vessel indirectly through the receiver surfaces and through the surfaces of the disposable vessel.

To ensure a uniform input of heat via the heating elements into the disposable vessel, the heating elements preferably extend over the entire length of the receiver, and also from the bottom thereof in the direction of the upper opening of the receiver, to such an extent that the heating elements reach almost, preferably at least, to the height of the maximum liquid level in the disposable vessel inserted in the receiver. The resistance heater controls the temperature of the water in the disposable vessel indirectly via the receiver surfaces and via the surface of the disposable vessel. The resistance heater is not an essential component of the water bath, but it is generally incorporated.

To substantially suppress a direct input of heat into the interior of the incubator through the heating elements, the heating elements in an advantageous embodiment of the invention are accommodated in a closed housing, wherein the receiver surfaces, on the rear sides of which the heating elements are fastened, form a component part of the housing. The air in the closed housing then has a heat-insulating function. In addition, heat-insulating materials can be arranged in the housing.

The disposable vessel converges at the end faces into the weld seams connecting the lateral vessel walls. By the protrusion of the disposable vessel, or by the end faces of the disposable vessel also being adapted to the shape of the receiver, it is ensured that the entire surface area of the receiver surfaces is in contact with the disposable vessel. A direct input of heat into the interior through some of the receiver surfaces is thus avoided.

The fastenings for fixing the disposable vessel comprise openings, which are arranged along the longitudinal edges of the disposable vessel, and knobs, which engage in the openings and which are fastened along the longitudinal edges of the disposable vessel on the receiver or on the housing arranged underneath the receiver. The knobs are preferably made of stainless steel. The openings at the longitudinal edges of the disposable vessel can be incorporated as punched holes in a cost-effective punching operation. In the case of heated receiver surfaces, a good match of the flexible disposable vessel to the receiver is important for an optimum input of heat into the liquid. As the flexible disposable vessel is filled with liquid, the walls of the vessel are pressed onto the receiver surfaces by the force of gravity of the liquid. The fastening of the flexible disposable vessel at multiple points near the edge additionally prevents the formation of folds in the film that forms the vessel.

In order to fill the disposable vessel automatically with liquid and to regulate the liquid level in the disposable vessel, the liquid supply has a tube with a valve, which is opened and closed depending on the signal from a float switch, wherein the float body of the float switch is arranged on the receiver in such a way that it floats on the liquid surface in the disposable vessel.

The regulation of the liquid level ensures that the disposable vessel is not completely emptied or does not overflow. The use of a float switch is cost-effective and contributes to the reliability of the water bath. The tube of the liquid supply is connected to a liquid port in the interior of the incubator. The liquid port of the incubator is fed either from a water canister, which lies outside the incubator, or from a water conduit.

BRIEF DESCRIPTION OF THE DRAWINGS

The invention is explained in more detail below on the basis of an illustrative embodiment. In the figures.

DETAILED DESCRIPTION OF THE PREFERRED EMBODIMENTS

Figure 2:
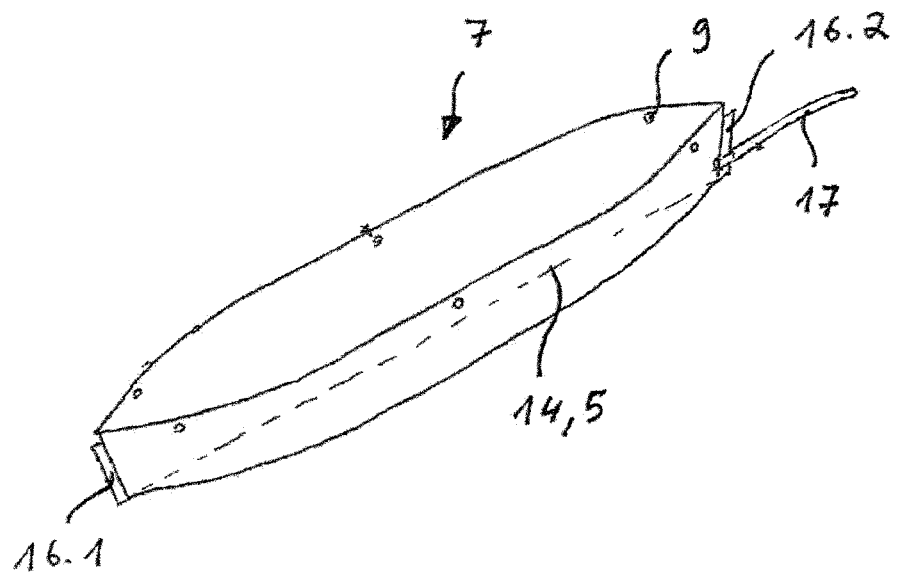
FIG. 2 is a perspective view of the finished disposable vessel.
Figure 3:
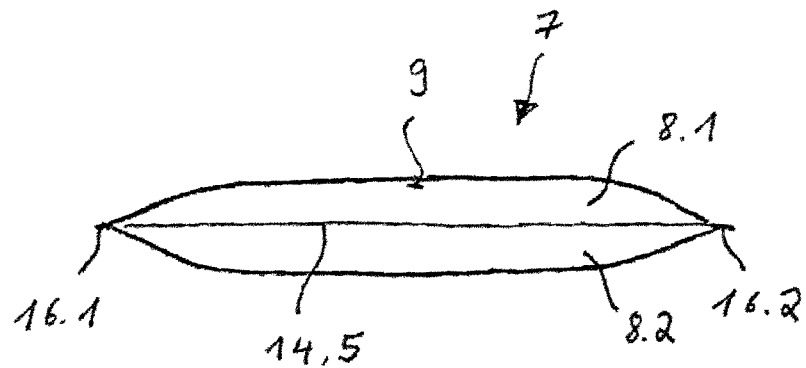
FIG. 3 is a plan view of the disposable vessel according to FIG. 2.
Figure 5:
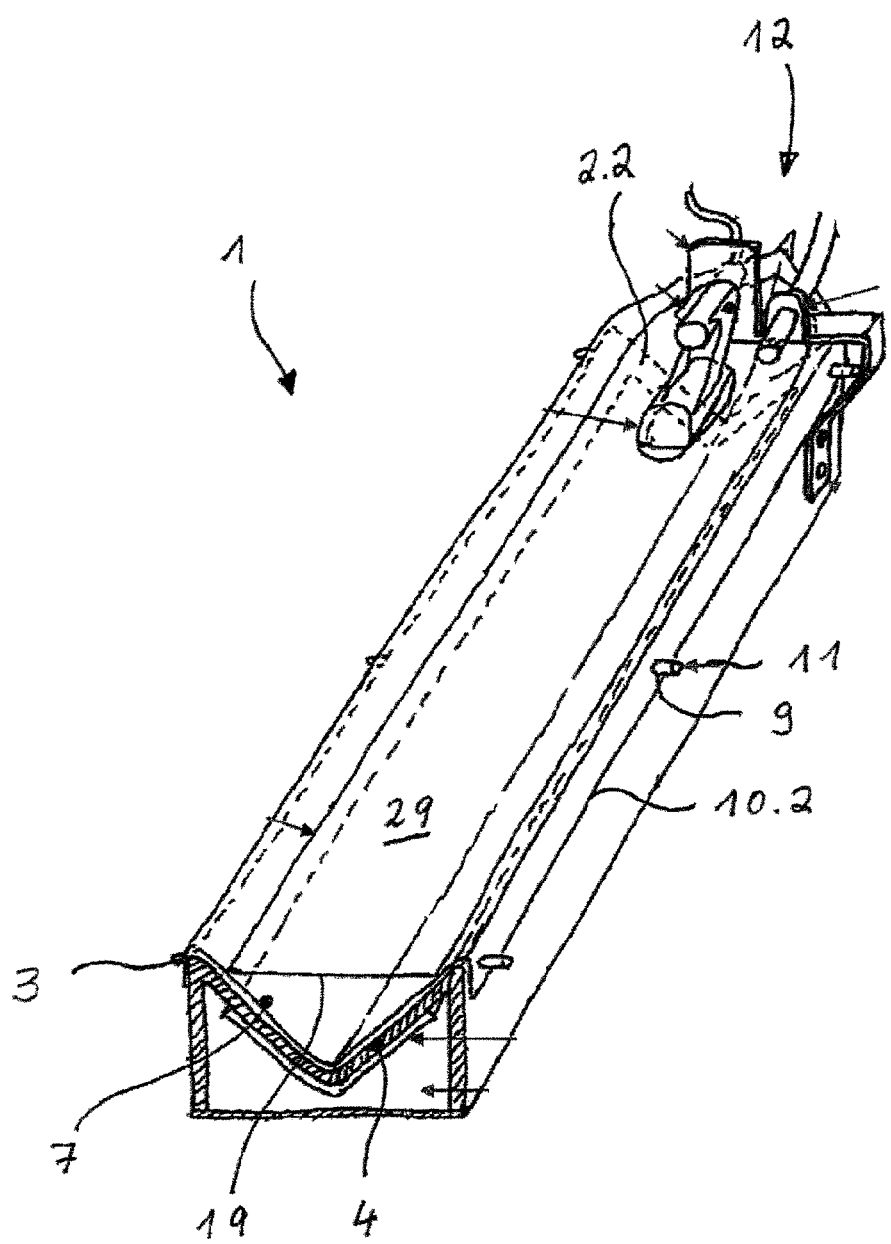
FIG. 5 is a perspective view of a water bath, partially in section.
Figure 6:
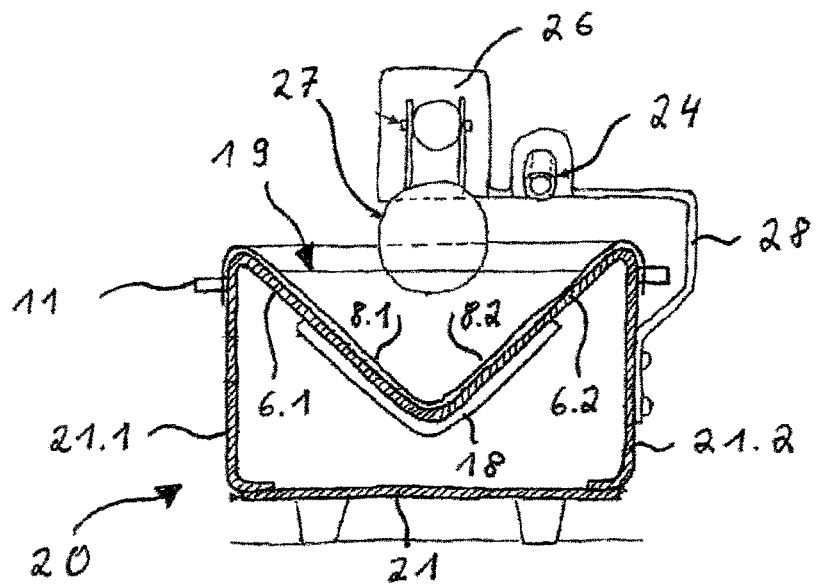
FIG. 6 is a cross section through the water bath according to FIG. 5.
Figure 7:
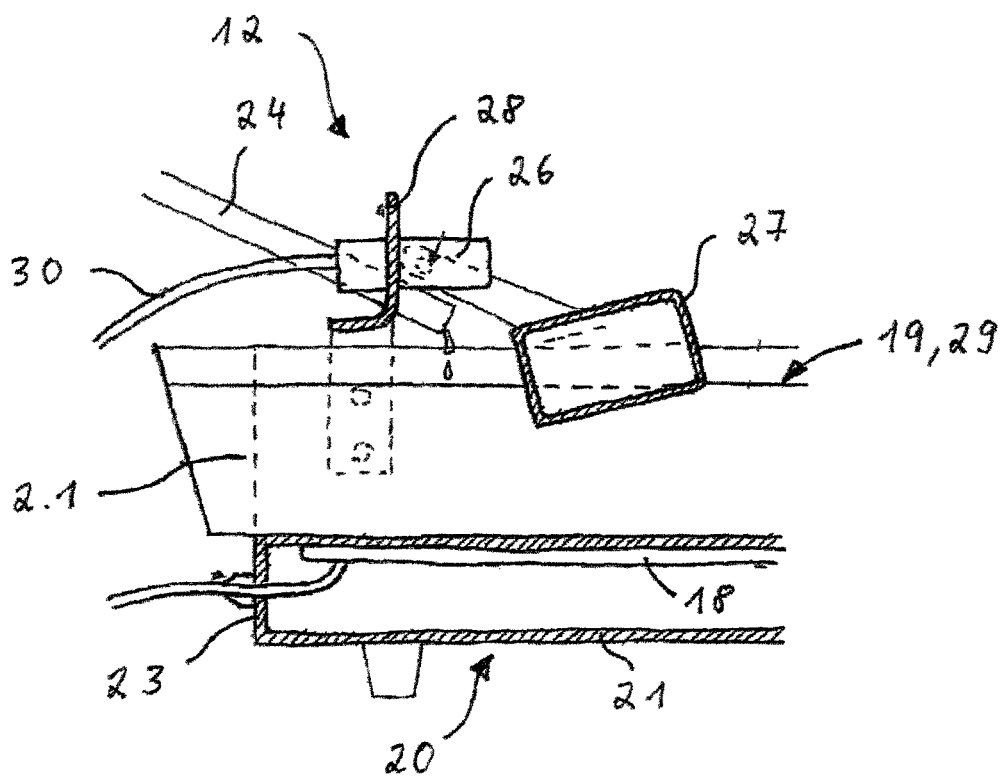
FIG. 7 is a longitudinal sectional view through an end face of the water bath according to FIG. 5.

FIGS. 5, 6 and 7 show a water bath 1 according to the invention for humidifying an interior of an incubator (not shown). The water bath 1 comprises as its main component parts a profiled V-shaped receiver 4, open at the end faces 2.1, 2.2 and at the upper face 3, with two receiver surfaces 6.1, 6.2 extending in the longitudinal direction 5 (see FIGS. 1-3).

The receiver 4 receives a prefabricated and flexible disposable vessel 7 for liquid, open at the upper face 3, in particular for sterile water, wherein the vessel walls 8.1, 8.2 lie flush on the receiver surfaces 6.1, 6.2 of the receiver 4 (see FIG. 6).

Fastenings for fixing the disposable vessel 7 on the receiver 4 comprise openings 9 along the longitudinal edges 10.1, 10.2 of the disposable vessel 7, and knobs 11 which engage in the openings 9.

Furthermore, the water bath 1 according to the invention has a liquid supply 12, designed for filling the disposable vessel 7 and for regulating the liquid level in the disposable vessel 7.

Figure 1:
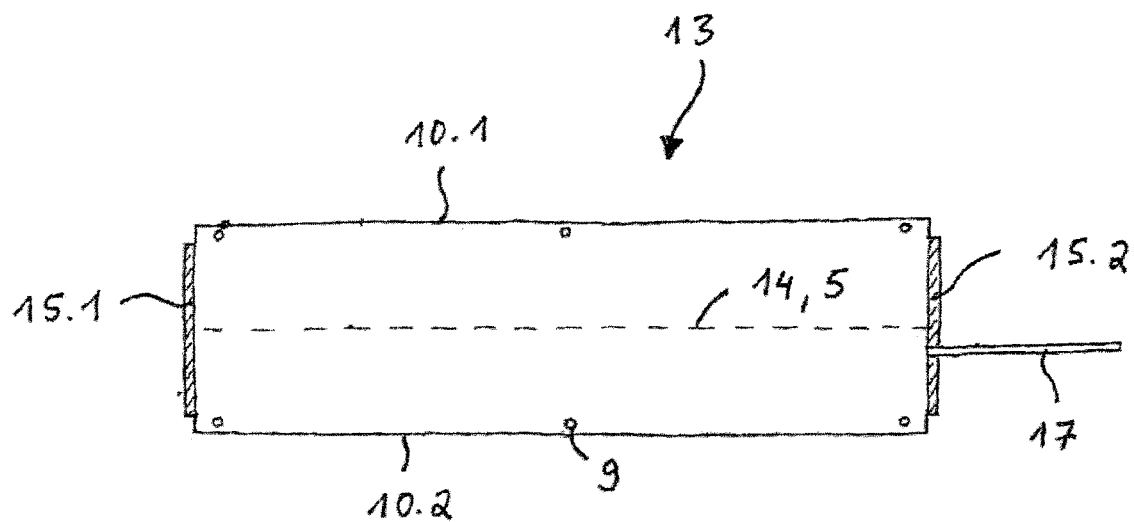
FIG. 1 shows a film for producing a disposable vessel.

FIG. 1 shows a substantially rectangular film 13, made of thermoplastic, for producing the disposable vessel 7. The film 13 is delimited by the longitudinal edges 10.1, 10.2, and by end-face edges 15.1, 15.2 that extend transversely with respect to the longitudinal edges 10.1, 10.2. The film 13 is folded along a longitudinal mid-line 14 and, at the end-face edges 15.1, 15.2, is provided with a weld seam 16.1, 16.2 (see FIG. 2) running from the longitudinal mid-line 14 in the direction of each of the longitudinal edges 10.1, 10.2. A drainage tube 17 is welded into the weld seam 16.2. The drainage tube 17 has a shut-off member (not shown), for example in the form of a disposable clamp, so that the water escapes from the drainage tube 17 only when the disposable vessel 7 is to be emptied.

With only two weld seams 16.1, 16.2 and one hole-punching operation to produce the openings 9, the disposable vessel 7 is able to be produced efficiently and at low cost.

Figure 4:
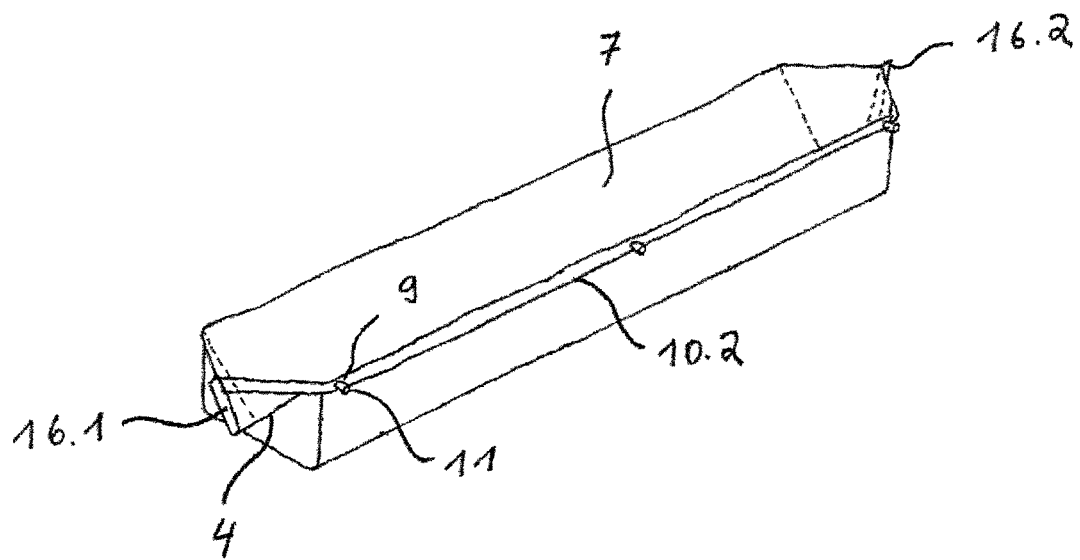
FIG. 4 is a perspective view of the disposable vessel in a V-shaped receiver.

It will be seen from FIG. 4 how the disposable vessel 7 produced is inserted into the receiver 4, and how it is fixed to the receiver 4 by means of the knobs 11 which engage in the openings 9 along the longitudinal edges 10.1, 10.2 of the film 13 or of the disposable vessel 7. Fixing the disposable vessel 7 using a multiplicity of knobs 11 has the effect that the disposable vessel 7 is positioned exactly with respect to the receiver 4 and lies, free from folds, with the vessel walls 8.1, 8.2 on the receiver surfaces 6.1, 6.2 of the receiver 4. Moreover, the knobs 11, together with the holes 9, facilitate simple mounting of the disposable vessel 7 in the receiver 4.

As shown in FIG. 6, a heating element 18 is arranged on the rear of the two receiver surfaces 6.1, 6.2. The heating element 18 is an electrical resistance heater, which is configured as a mat and is affixed to the rear of the receiver surfaces 6.1, 6.2. The mat extends over almost the entire length of the receiver 4, and also from the bottom thereof in the direction of the upper face 3 of the water bath 1, to such an extent that the heating element 18 reaches almost to the height of the maximum liquid level 19 in the disposable vessel 7.

In order to substantially suppress a direct input of heat into the interior of the incubator through the heating element 18, the heating element 18 is accommodated in a closed housing 20, which is delimited by a housing floor 21, side walls 21.1, 21.2, end walls 23 and the profiled V-shaped receiver 4 (see FIGS. 6 and 7). The knobs 11 for fixing the disposable vessel 7 on the receiver 4 are fastened to the side walls 21.1, 21.2 of the housing 20.

FIGS. 6 and 7 shows that the liquid supply 12 of the water bath 1 has a tube 24 with an electrically actuated valve. The tube 24 is connected to a liquid port (not shown) in the interior of the incubator, which liquid port is fed from an external water conduit. The valve is opened and closed depending on the signal from a float switch 26. A float body 27 of the float switch 26 is mounted rotatably on a holder 28 which is screwed onto the housing 20. The float body 27 of the float switch 26 floats on the liquid surface 29 in the disposable vessel 7 and, depending on the liquid level in the disposable vessel 7, outputs a signal via a signal cable 30 to a controller, which opens the electrically actuated valve when there is a minimum liquid level and closes said valve when the maximum liquid level 19 is reached.

The water bath 1 according to the invention is placed on the floor in the interior of the incubator. The disposable vessel 7, open at the upper face, is located underneath a condensation unit which recondenses the water in the gas mixture in the incubator and thereby permits regulation of the relative humidity of the gas mixture. The recondensed water drips directly back into the disposable vessel 7.

For inserting the disposable vessel 7 into the receiver 4 and removing it therefrom, it is not necessary to take the receiver 4 out of the incubator.

To empty the disposable vessel 7 before it is removed, the clamp of the drainage tube 17 is manually opened. The water running off can either be collected in a separate receptacle or can be discharged through a drainage system arranged in the incubator near the bottom thereof.

LIST OF REFERENCE SIGNS 1 water bath
2.1, 2.2 end faces
3 upper face
4 receiver
5 longitudinal direction
6.1, 6.2 receiver surfaces
7 disposable vessel
8.1, 8.2 vessel walls
9 openings 10.1, 10.2 longitudinal edges
11 knobs
12 liquid supply
13 film
14 longitudinal mid-line
15.1, 15.2 end-face edges
16.1, 16.2 weld seam
17 drainage tube
18 heating element
19 maximum liquid level
20 housing
21 housing floor
22.1, 22.2 side walls
23 end wall
24 tube
26 float switch
27 float body
27 holder
29 liquid surface
30 signal cable

What is claimed is:

1. A water bath for humidifying an interior of an incubator, comprising:
   a profiled receiver having a constant cross section in a longitudinal direction of the profiled receiver, being open at least at an upper face, and having receiver surfaces extending in the longitudinal direction,
   a prefabricated disposable vessel for holding liquid, the disposable vessel being open at the upper face and having vessel walls that lie flush on the receiver surfaces of the receiver,
   fastenings for fixing the disposable vessel on the receiver, and
   a liquid supply for filling the disposable vessel with liquid,
   wherein the disposable vessel includes a substantially rectangular film made of a flexible material having longitudinal edges and being folded along a longitudinal mid-line, the disposable vessel further including end faces and weld seams at the respective end faces running from the longitudinal mid-line to each of the longitudinal edges of the film.

2. The water bath according to claim 1, further comprising a drainage tube with a shut-off member welded into one of the weld seams.

3. The water bath according to claim 1, wherein the receiver has a V-shaped cross section.

4. The water bath according to claim 1, wherein the receiver surfaces of the receiver are heated.

5. The water bath according to claim 4, further comprising at least one heating element arranged on a rear side of the receiver surfaces.

6. The water bath according to claim 5, wherein the at least one heating element is accommodated in a closed housing, and the receiver surfaces are a component part of the housing.

7. The water bath according to claim 1, wherein the disposable vessel protrudes slightly beyond the receiver at both end faces of the receiver.

8. The water bath according to claim 1, wherein the fastenings include openings arranged along the longitudinal edges of the disposable vessel and knobs that engage in the openings.

9. The water bath according to claim 1, wherein the liquid supply includes a tube with a valve and a float switch, the valve is opened or closed depending on a signal from the float switch, a float body of the float switch floats on a liquid surface in the disposable vessel.

10. The water bath according to claim 1, wherein the disposable vessel is made of thermoplastic.

11. The water bath according to claim 1, wherein the profiled receiver is open at the end faces and the upper face.

* * * * *